(12) United States Patent
Kansal et al.

(10) Patent No.: US 8,097,754 B2
(45) Date of Patent: Jan. 17, 2012

(54) SYNTHESIS OF (S)-(+)-3-(AMINOMETHYL)-5-METHYL HEXANOIC ACID

(75) Inventors: Vinod Kumar Kansal, Haryana (IN); Brijnath P. Chaurasia, Uttar Pradesh (IN); Anand Prakash Tiwari, Uttar Pradesh (IN); Shivaji Haribhau Shelke, Maharashtra (IN)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 936 days.

(21) Appl. No.: 12/079,225

(22) Filed: Mar. 24, 2008

(65) Prior Publication Data

US 2008/0306292 A1    Dec. 11, 2008

Related U.S. Application Data

(60) Provisional application No. 60/919,575, filed on Mar. 22, 2007, provisional application No. 60/932,317, filed on May 29, 2007.

(51) Int. Cl.
C07C 247/12    (2006.01)
(52) U.S. Cl. ................... 562/443; 564/193; 564/194
(58) Field of Classification Search .................. None
See application file for complete search history.

(56) References Cited

U.S. PATENT DOCUMENTS

| | | | |
|---|---|---|---|
| 5,010,189 A | 4/1991 | Herold et al. | |
| 5,599,973 A | 2/1997 | Silverman et al. | |
| 5,616,793 A | 4/1997 | Huckabee et al. | |
| 5,629,447 A | 5/1997 | Huckabee et al. | |
| 5,637,737 A | 6/1997 | Andres et al. | |
| 5,637,767 A | 6/1997 | Grote et al. | |
| 6,001,876 A | 12/1999 | Singh | |
| 6,197,819 B1 | 3/2001 | Silverman et al. | |
| 6,333,198 B1 | 12/2001 | Edmeades et al. | |
| 6,359,169 B1 | 3/2002 | Silverman et al. | |
| 6,488,964 B2 | 12/2002 | Bruna et al. | |
| 6,580,003 B2 | 6/2003 | Deng et al. | |
| 6,642,398 B2 | 11/2003 | Belliotti et al. | |
| 6,833,458 B2 | 12/2004 | Liu et al. | |
| 6,891,059 B2 | 5/2005 | Burk et al. | |
| 6,924,377 B2 | 8/2005 | Blazecka et al. | |
| 7,141,695 B2 | 11/2006 | Przewosny et al. | |
| 7,446,220 B2 | 11/2008 | Kansal et al. | |
| 7,462,738 B2 | 12/2008 | Hedvati et al. | |
| 2001/0016665 A1 | 8/2001 | Grote et al. | |
| 2003/0212290 A1 | 11/2003 | Burk et al. | |
| 2003/0225149 A1 | 12/2003 | Blazecka et al. | |
| 2005/0222464 A1 | 10/2005 | Hoge, II | |
| 2005/0228190 A1 | 10/2005 | Bao et al. | |
| 2005/0283023 A1 | 12/2005 | Hu et al. | |
| 2006/0270871 A1 | 11/2006 | Khanduri et al. | |
| 2007/0073085 A1 | 3/2007 | Hedvati et al. | |
| 2007/0191636 A1 | 8/2007 | Kansal et al. | |
| 2007/0197827 A1 | 8/2007 | Kansal et al. | |
| 2008/0014280 A1 | 1/2008 | Kumar et al. | |
| 2008/0311635 A1 | 12/2008 | Riva et al. | |
| 2009/0143615 A1 | 6/2009 | Allegrini et al. | |

FOREIGN PATENT DOCUMENTS

| | | |
|---|---|---|
| CN | 1 634 869 | 7/2005 |
| CZ | 297 970 | 3/2007 |
| EP | 1 992 609 | 11/2008 |
| EP | 2 067 768 | 6/2009 |
| WO | WO 96/38405 A1 | 12/1996 |
| WO | WO 96/40617 A1 | 12/1996 |
| WO | WO 01/55090 A1 | 8/2001 |
| WO | WO 2005/100580 | 10/2005 |
| WO | WO 2006/000904 A2 | 1/2006 |
| WO | WO 2006/008640 | 1/2006 |
| WO | WO 2006/110783 | 10/2006 |
| WO | WO 2006/122255 | 11/2006 |
| WO | WO 2006/122258 | 11/2006 |
| WO | WO 2006/136087 | 12/2006 |
| WO | WO 2007/035789 | 3/2007 |
| WO | WO 2007/035890 | 3/2007 |
| WO | WO 2007/139933 | 12/2007 |
| WO | WO 2007/143113 | 12/2007 |
| WO | WO 2008/004044 | 1/2008 |
| WO | WO 2008/007145 | 1/2008 |
| WO | WO 2008/009897 | 1/2008 |
| WO | WO 2008/118427 | 10/2008 |
| WO | WO 2009/010554 | 1/2009 |

OTHER PUBLICATIONS

International Search Report and Written Opinion of ISA, dated Oct. 30, 2008, from corresponding International Application No. PCT/US2008/003898.
Burk et al., "An Enantioselective Synthesis of (S)-(+)-3-Aminomethyl-5-methylhexanoic Acid via Asymmetric Hydrogenation", J. Org. Chem., 68(14): 5731-5734 (2003).
Lin et al., "Chiral HPLC Separations for Process Development of S-(+)-Isobutyl GABA, A Potential Anti-Epileptic Agent", J. Liq. Chrom. & Rel. Technol., 19(16), 2699-2708 (1996).
Liu et al., "Asymmetric syntheses of trans-3,4-disubstituted 2-piperidinones and piperidines," Tetrahedron: Asymmetry, 12:419-426 (2001).

(Continued)

Primary Examiner — Daniel Sullivan
Assistant Examiner — Yevegeny Valenrod
(74) Attorney, Agent, or Firm — Kenyon & Kenyon LLP (57) ABSTRACT

Provided are syntheses of (S)-(+)-3-(aminomethyl)-5-methylhexanoic acid, (S)-Pregabalin via a chiral intermediate of the following formula 4

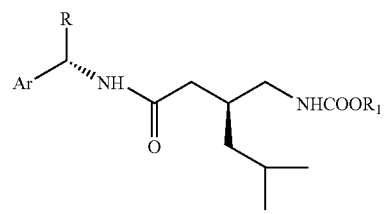

wherein Ar is a $C_{6-10}$ aromatic group, R is a straight or branched $C_{1-4}$ alkyl, ester, or carboxylic acid, and $R_1$ is a straight or branched $C_{1-5}$ alkyl, aralkyl, or substituted aralkyl.

49 Claims, 1 Drawing Sheet

OTHER PUBLICATIONS

Serfass et al., "General Synthesis of 3-Substitued Alkenyl GABA as Potential Anticonvulsants," Bioorganic & Medicinal Chemistry Letters 8 (1998) 2599-2602.

Yuen et al., "Enantioselective Synthesis of PD144723: A Potent Stereospecific Anticonvulsant", Bioorganic & Medicinal Chemistry Letters, 4(6), 823-826(1994).

Andruszkiewicz and Silverman, "A Convenient Synthesis of 3-Alkyl-4-Aminobutanoic Acids," *Synthesis*, 953-955 (1989).

Barnes, D.M., et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram," *J. Am. Chem. Soc.*, 124(44): 13097-13105 (2002).

Berner et al. "Asymmetric Michael Additions to Nitroalkenes," *European Journal of Organic Chemistry*, 1877-1894 (2002).

Cason, J. et al., "Branched-Chain Fatty Acids. XXVII. Further Study of the Dependence of Rate of Amide Hydrolysis on Substitution near the Amide Group. Relative Rates of Hydrolysis of Nitrile to Amide and Amide to Acid," *J. Org. Chem.*, 18(9): 1129-1136 (1953).

Chen, AO et al., "Synthesis of Pregabalin," *Zhongguo YiYao Gongye Zazhi*, 35(4): 195-196 (2004).

Colonge et al., "Preparation De Pyrrolidones-2 et de Gamma-Aminoacides," *Bulletin De La Societe Chimique De France, Societe Francaise De Chimie*, 598-603 (1962).

Day and Thorpe, "The Formation and Reactions of Imino-compounds. Part XX. The Condensation of Aldehydes with Cyanoacetamide," *J. Chem. Soc.*, 117: 1465-1474 (1920).

Hoekstra, M.S. et al., "Chemical Development of Cl-1008, an Enantiomerically Pure Anticonvulsant," *Organic Process Research and Development*, 1(1): 26-38 (1997).

Karanewsky, D.S. et al., "Practical Synthesis of an Enantiomerically Pure Synthon for the Preparation of Mevinic Acid Analogues," *J. Org. Chem.*, 56(11): 3744-3747 (1991).

Li, H. et al., "Highly Enantioselective Catalytic Conjugate Addition of Malonate and β-Ketoester to Nitroalkenes: Asymmetric C-C Bond Formation with New Bifunctional Organic Catalysts Based on Cinchona Alkaloids," *J. Am. Chem. Soc.*, 126(32): 9906-9907 (2004).

Martin et al., "Pregabalin," *Drugs of the Future*, 24(8): 862-870 (1999).

Okino, T. et al., "Enantio- and Diastereoselective Michael Reaction of 1,3-Dicarbonyl Compounds to Nitroolefins Catalyzed by a Bifunctional Thiourea," *J. Am. Chem. Soc.*, 127(1): 119-125 (2005).

Sammis, G.M. et al., "Highly Enantioselective Catalytic Conjugate Addition of Cyanide to α,β-Unsaturated Imides", *J. Am. Chem. Soc.*, 125(15): 4442-43 (2003).

Shintani et al., "Highly Enantioselective Desymmetrization of Anhydrides by Carbon Nucleophiles: Reactions of Grignard Reagents in the Presence of (−)-Sparteine," *Ansewandte Chemie, International Edition*, 41(6): 1057-1059 (2002).

Snyder et al., Introduction to Modern Liquid Chromatography, 549-572 (2d ed., John Wiley & Sons, 1979).

Strobel et al., Chemical Instrumentation: A Systematic Approach, 391-393, 879-894, 922-925, 953 (3d ed. 1989).

Theisen, P.D. et al., "Prochiral Recognition in the Reaction of 3-Substituted Glutaric Anhydrides with Chiral Secondary Alcohols," *J. Org. Chem.*, 58(1): 142-146 (1993).

Verma, Rekha et al., "Desymmetrization of prochiral anhydrides with Evans' oxazolidinones: an efficient route to homochiral glutaric and adipic acid derivatives," *J. Chem. Soc., Perkin Transactions 1: Organic and Bio-Organic Chemistry*, 257-264 (1999).

Yamamoto et al., "Stereoselective Synthesis of (E)-Alkylidenesuccinates by Palladium-catalyzed Carbonylation," *Bull. Chem. Soc. Japan*, 58(11): 3397-3398 (1985).

FIG. 1

SYNTHESIS OF (S)-(+)-3-(AMINOMETHYL)-5-METHYL HEXANOIC ACID

CROSS-REFERENCE TO RELATED APPLICATIONS

This application claims the benefit of U.S. provisional application Ser. Nos. 60/919,575, filed Mar. 22, 2007 and 60/932,317, filed May 29, 2007, hereby incorporated by reference.

FIELD OF THE INVENTION

The invention encompasses syntheses of (S)-(+)-3-(aminomethyl)-5-methylhexanoic acid, (S)-Pregabalin.

BACKGROUND OF THE INVENTION

(S)-Pregabalin, (S)-(+)-3-(aminomethyl)-5-methylhexanoic acid, a compound having the chemical structure, is also known as γ-amino butyric acid or (S)-3-isobutyl GABA. (S)-Pregabalin, marketed under the name LYRICA®, has been found to activate GAD (L-glutamic acid decarboxylase). (S)-Pregabalin has a dose dependent protective effect on seizure, and is a CNS-active compound. (S)-Pregabalin is useful in anticonvulsant therapy, due to its activation of GAD, promoting the production of GABA, one of the brain's major inhibitory neurotransmitters, which is released at 30 percent of the brains synapses. (S)-Pregabalin has analgesic, anticonvulsant, and anxiolytic activity.

Several processes for the synthesis of (S)-Pregabalin are known. For example, U.S. Pat. No. 5,599,973 ("'973 patent") discloses the preparation of (S)-Pregabalin using a stoichiometric amount of (4R,5S)-(+) 4-methyl-5-phenyl-2-oxazolidinone as a chiral auxiliary that may be recycled. See, e.g., '973 patent, col. 14, 1.29 to col. 18, 1.23 (example 1). In general, however, the route disclosed in the '973 patent is of limited use on an industrial scale, principally due to the low temperature required for the reaction (e.g., −78° C.), the use of pyrophoric reagent (e.g., butyl lithium), and a low overall yield (e.g., 59%, 65%).

U.S. Publication No. 2003/0212290 ("'290 publication") discloses the synthesis of (S)-Pregabalin by an asymmetric hydrogenation of a cyano-substituted olefin of formula 7, to produce a cyano precursor of (S)-3-(aminomethyl)-5-methyl hexanoic acid of formula 8, which is further reduced to obtain (S)-Pregabalin, as described in the following scheme.

However, the disclosed method requires the use of carbon monoxide under high pressure, raising serious problems in adapting this process for production scale.

Another process is disclosed by G. M. Sammis, et al., *J. Am. Chem. Soc.*, 125(15): 4442-43 (2003), in which an aluminum salen catalyst is used in the conjugate addition of hydrogen cyanide to α,β-unsaturated imides.

This process is also not practical for large scale production due to the use of highly poisonous reagents. In addition, the last reduction step requires high hydrogen pressure, which only adds to the difficulties required for adapting this process for use on an industrial scale.

International Publication WO 2006/110783 reports several processes for preparing (S)-Pregabalin via the following intermediate and its analogues wherein $R_1$ and $R_2$ are independently H, a straight or branched $C_{1-10}$ alkyl, $C_{6-10}$ aryl, or $C_{3-6}$ allyl.

U.S. Publication Nos. 2007/0191636 and 2007/0197827 also disclose processes for preparing (S)-Pregabalin.

Thus, there is a need in the art for additional process for the preparation of (S)-Pregabalin that provide (S)-Pregabalin in high quality, and that can be adapted to large (industrial) scale production.

SUMMARY OF THE INVENTION

In one embodiment, the invention encompasses a compound of the following formula 5 wherein Ar is a $C_{6-10}$ aromatic group, and R is a straight or branched $C_{1-4}$ alkyl, ester, or carboxylic acid.

In another embodiment, the invention encompasses a process for preparing (S)-Pregabalin via the compound of claim 1.

In another embodiment, the invention encompasses a process for preparing (S)-Pregabalin comprising: (a) combining a compound of the following formula 4 with an acid and a phenol of formula 2;

and (b) recovering (S)-Pregabalin, wherein Ar is a $C_{6-10}$ aromatic group, R is a straight or branched $C_{1-4}$ alkyl, ester, or carboxylic acid, $R_1$ is a straight or branched $C_{1-5}$ alkyl, aralkyl, or substituted aralkyl, $R_2$ is H, alkyl, alkoxy, halogen, or mercapto, $R_4$ is H, alkyl or halogen, and the ring Z is a 5-8-membered ring containing carbon and optionally at least one nitrogen, sulfur or oxygen.

The compound of formula 4 may be prepared by a process comprising combining a compound of formula 1 with bromine and a base in a straight or branched alkyl alcohol.

Alternatively, the compound of formula 4 may be prepared by a process comprising: (i) combining a compound of formula 3 with an azide nucleophile to obtain a compound of formula 5, and (ii) combining the compound of formula 5 with an alcohol to obtain the compound of formula 4, wherein Ar is a $C_{6-10}$ aromatic group, R is a straight or branched $C_{1-4}$ alkyl, ester, or carboxylic acid, and X is a leaving group.

DETAILED DESCRIPTION OF THE INVENTION

In one embodiment, the invention encompasses an azide of the following formula 5 wherein Ar is a $C_{6-10}$ aromatic group, and R is a straight or branched $C_{1-4}$ alkyl, ester, or carboxylic acid. Preferably, Ar is phenyl and R is ethyl.

The azide of formula 5 is used as an intermediate in the synthesis of (S)-Pregabalin as will be demonstrated below.

The invention also encompasses asymmetric syntheses of (S)-Pregabalin via a chiral intermediate of the following formula 4 wherein Ar is a $C_{6-10}$ aromatic group, R is a straight or branched $C_{1-4}$ alkyl, ester, or carboxylic acid, and $R_1$ is a straight or branched $C_{1-5}$ alkyl, aralkyl, or substituted aralkyl. These asymmetric syntheses produce (S)-Pregabalin with relatively high enantiomeric and chemical purity, while avoiding an optical resolution step. These asymmetric syntheses are also economical and easy to conduct, and thus suitable for large scale production. These asymmetric syntheses can be illustrated by the following Scheme 1.

bromobenzene, and fluorobenzene. Preferred alkylated phenyls are either toluene or ethylbenzene. Preferably, the carboxylic acid substituent is —COOH, —CH$_2$COOH, —CH(CH$_3$)COOH or —C(CH$_3$)$_2$COOH. Preferably the ester substituent is a methylester, ethylester, isopropylester, n-butylester, isobutyl, or t-butyl derivative of one of the above-listed carboxylic acid substituents. The most preferred $C_{6-10}$ aromatic group is phenyl.

Preferably, the $C_{1-4}$ alkyl is methyl, ethyl, isopropyl, n-butyl, isobutyl or t-butyl, and more preferably methyl.

Preferably, the ester is a $C_{2-4}$ ester.

Preferably, the carboxylic acid is a $C_{1-2}$ carboxylic acid.

Preferably, the straight or branched $C_{1-5}$ alkyl is methyl.

Preferably, the aralkyl is a $C_{7-10}$ aralkyl, and more preferably benzyl.

Typically, the leaving group is derived from an acid activating agent. The term "acid activating agent" refers to a substance containing a group that activates a carbonyl group, i.e., makes the carbonyl group more susceptible to nucleowherein Ar is a $C_{6-10}$ aromatic group, R is a straight or branched $C_{1-4}$ alkyl, ester, or carboxylic acid, $R_1$ is a straight or branched $C_{1-5}$ alkyl, aralkyl, or substituted aralkyl, and X is a leaving group.

Preferably, the $C_{6-10}$ aromatic group is naphthyl, phenyl, substituted phenyl, or substituted naphthyl, more preferably phenyl. Preferably, the substituted phenyl is a phenyl group substituted with at least one of alkoxy, halogen, alkyl, carboxylic acid, or ester. A preferred alkoxy phenyl is methoxyphenyl. Preferred halogenated phenyls are chlorobenzene, philic attack, when attached to it. Preferably, the leaving group is a halogen or a mixed anhydride. Preferably, the halogen is either Cl or Br. Preferably, the mixed anhydride is —OCOR$_3$, wherein —OCOR$_3$ is derived from a haloformate, an acid halide, or an anhydride, such as acetic anhydride, di-t-butyl dicarbonate ("(BOC)$_2$O"), and the like. Preferably, $R_3$ is an alkyl group.

One synthetic path follows the conversion of compound of formula 1 to the compound of formula 4 by a Hoffman reaction as depicted below wherein Ar is a $C_{6-10}$ aromatic group, R is a straight or branched $C_{1-4}$ alkyl, ester, or carboxylic acid, and $R_1$ is a straight or branched $C_{1-5}$ alkyl, aralkyl, or substituted aralkyl.

The compound of formula 1 can be prepared, for example, according to the process disclosed in U.S. Publication No. 2007/0197827 and its international counterpart International Publication No. WO 2007/035890, both of which are hereby incorporated by reference.

The Hoffman reaction comprises combining the compound of formula 1 with bromine and a base in a straight or branched alkyl alcohol, aralkyl alcohol, or substituted aralkyl alcohol to obtain a mixture, and heating the mixture to obtain the compound of formula 4.

Typically, the compound of formula 1 and the alcohol are initially combined to obtain a solution. Preferably, the aralkyl alcohol is a $C_{7-10}$ aralkyl alcohol, and more preferably benzyl alcohol. Preferably, the alcohol is a straight or branched alkyl alcohol. Preferably, the straight or branched alkyl alcohol is methyl, ethyl, isopropyl, n-butyl, isobutyl, or t-butyl alcohol, and more preferably methanol or ethanol.

Then, the solution is preferably cooled prior to the addition of the base. Preferably, the cooling is to a temperature of about 10° C. to about −30° C., and more preferably to about 5° C. to about 0° C.

Preferably, the base is either a metal alkoxide or a metal hydroxide. Preferably, the metal alkoxide is a $C_{1-4}$ alkoxide, and more preferably is selected from the group consisting of sodium ethoxide, sodium methoxide, potassium methoxide, potassium ethoxide, and potassium tert butoxide. Preferably, the metal hydroxide is selected from the group consisting of lithium hydroxide, sodium hydroxide and potassium hydroxide. The more preferred base is either sodium hydroxide or potassium hydroxide Typically, the addition of the base provides a first mixture. Typically, this mixture is cooled prior to the addition of the bromine because the addition of the bromine causes an exothermic reaction. Preferably, the mixture is cooled to a temperature of about 10° C. to about −30° C., and more preferably to about 15° C. to about −25° C.

Typically, the addition of the bromine provides a second mixture, which is maintained while cooling as described above before being heated. Preferably, the second mixture is maintained with cooling for about 0.5 hour to about 4 hours, and more preferably for about 1 to about 2 hours.

Preferably, the second mixture is heated to a temperature of about 50° C. to about 70° C., and more preferably to a temperature of about 55° C. to about 65° C. Usually, the heated mixture is maintained for a period of time, during which the formation of the compound of formula 4 is expected to occur. Preferably, the heated mixture is maintained for about 0.5 hour to about 4 hours, and more preferably for about 1 hour to about 4 hours.

The compound 4 thus obtained may be recovered prior to being hydrolyzed to obtain (S)-Pregabalin. The compound of formula 4 may be recovered, for example, by evaporating the solvent; extracting with a solvent selected from a group consisting of dichloromethane, ethylacetate and toluene; and evaporating the solvent.

The recovered compound of formula 4 may have a purity of at least about 80% area by HPLC, preferably about 90% to about 100% area by HPLC, and more preferably about 92% to about 100% area by HPLC.

The second synthetic path follows the conversion of compound of formula 3 to the compound of formula 4:

wherein Ar is a $C_{6-10}$ aromatic group, R is a straight or branched $C_{1-4}$ alkyl, ester, or carboxylic acid, $R_1$ is a straight or branched $C_{1-5}$ alkyl, aralkyl, or substituted aralkyl, and X is a leaving group as described above.

The compound of formula 3 can be prepared, for example, according to the process disclosed in U.S. Publication No. 2007/0197827 and its international counterpart International Publication No. WO 2007/035890. The compound of formula 3 can be recovered prior to being converted to the compound of formula 4 or can be converted in-situ to the compound of formula 4.

The conversion comprises combining the compound of formula 3 with an azide nucleophile to obtain the compound of formula 5, and combining the compound of formula 5 with an alcohol to obtain the compound of formula 4.

Typically, the azide nucleophile is a substance containing a nucleophilic "$N_3$" group. Examples of such substances include, but are not limited to, $NaN_3$, diphenylphosphoryl azide, trialkyl silyl azide, trialkyl tin azide, and like metal azides. More preferably, the azide nucleophile is $NaN_3$.

The azide nucleophile can be provided in the form of a solid or in an aqueous or organic solution. Typically, the compound of formula 3 is combined with the azide nucleophile at a low temperature. Preferably, the compound of formula 3 is combined with the azide nucleophile at a temperature of about 30° C. to about −30° C., and more preferably at about −10° C. to about −20° C.

The reaction between the azide nucleophile and the compound of formula 3 typically leads to a slurry. The slurry, usually, further comprises an organic solvent. This organic solvent is either the solvent from the reaction used to produce the compound of formula 3 when the reaction is one-pot, or a new solvent used to dissolve the compound of formula 3 when the reaction begins with a recovered compound of formula 3.

Preferably, the organic solvent is selected from the group consisting of aromatic hydrocarbons, aliphatic hydrocarbons, ethers and ketones. Preferably, the aromatic hydrocarbon is a $C_{6-10}$ aromatic hydrocarbon, and more preferably toluene, xylene or ethyl benzene. Preferably, the aliphatic hydrocarbon is a $C_{6-10}$ aliphatic hydrocarbon, and more preferably either hexane or heptane. Preferably, the ether is a $C_{3-9}$ ether, and more preferably diethylether, diisopropylether or t-butylmethyl ether. Preferably, the ketone is a $C_{3-6}$ ketone, and more preferably acetone, methylethyl ketone or methylisobutyl ketone. The more preferred solvent is acetone or toluene.

The above slurry is typically maintained for a sufficient time to provide the compound of formula 5. Preferably, the slurry is maintained for about 0.5 hour to about 4 hours, more preferably for about 0.5 hour to about 2 hours, and most preferably for about 1 hour to about 2 hours.

The slurry of the compound of formula 5 may be used to synthesize the compound of formula 4 directly, without isolation of the compound of formula 5 from the slurry. Alternatively, the compound of formula 5 is separated from the slurry by addition of water and an organic solvent prior to its use in the synthesis of the compound of formula 4. Preferably, the organic solvent is the same as described above. The water dissolves the inorganic salts while the compound of formula 5 is transferred into the organic phase. Optionally, the aqueous phase can be further extracted with the organic solvent to increase the yield of the compound of formula 5.

Figure 1:
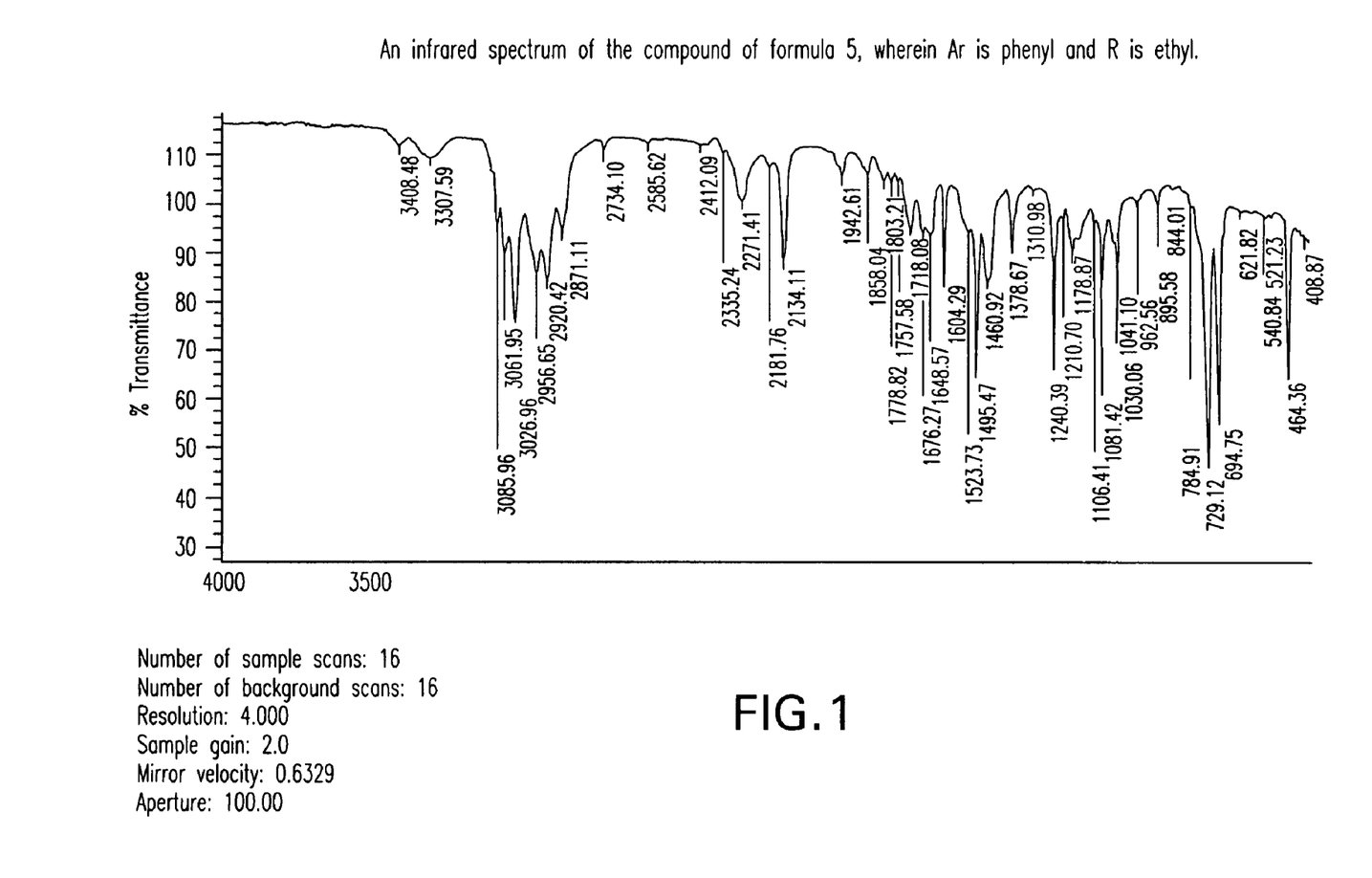
FIG. 1 illustrates an infrared spectrum of the compound of formula 5, wherein Ar is phenyl and R is ethyl.

The compound of formula 5 can be characterized by an infrared spectrum having an azide peak at 2134 cm$^{-1}$. An infrared spectrum for a representative compound of formula 5, wherein Ar is phenyl and R is ethyl, is illustrated in FIG. 1.

The organic phase having the compound of formula 5 is then combined with an alcohol to obtain the compound of formula 4. Preferably, the organic phase is added slowly to the alcohol, more preferably the organic phase is added over a period of about 0.5 to about 10 hours, and most preferably over a period of about 0.5 hour to about 4 hours. Preferably, the combination is done while heating the alcohol, more preferably while heating the alcohol to a temperature of about 50° C. to about 110° C., and most preferably while heating the alcohol to a temperature of about 50° C. to about 70° C. Preferably, the alcohol is in the form of a solution of the alcohol in an organic solvent. Preferably, the solvent is the same as mentioned above. Preferably, the alcohol is a $C_{1-5}$ alcohol, and more preferably methanol, ethanol, isopropanol, t-butanol, n-butanol, isobutanol, or neopentylalcohol. More preferably, the alcohol is either methanol or ethanol. The heated combination is then maintained, preferably, for about 0.5 to about 6 hours to provide the compound of formula 4. More preferably, the heated combination is maintained for about 0.5 to about 4 hours, and most preferably for about 2 to about 4 hours, to provide the compound of formula 4.

The compound of formula 4 may be recovered prior to being hydrolyzed to obtain (S)-Pregabalin. The compound of formula 4 may be recovered, for example, by evaporating the solvents.

The recovered compound of formula 4 may have a purity of at least about 85% area by HPLC, preferably about 92% to about 100% area by HPLC, and more preferably about 95% to about 100% area by HPLC.

The compound of formula 4 can then be converted to (S)-Pregabalin, for example, by the process disclosed in U.S. Publication No. 2007/0197827 and its international counterpart International Publication No. WO 2007/035890.

Typically, the conversion of the compound of formula 4 to (S)-Pregabalin is done by hydrolyzing the amide and amine group. The hydrolysis of the compound of formula 4 to give (S)-pregabalin can be done without isolating the compound of formula 4, i.e., a one-pot process.

The hydrolysis comprises combining the compound of formula 4, with an acid and a phenol of formula 2;

and recovering the (S)-Pregabalin thus obtained, wherein Ar is a $C_{6-10}$ aromatic group, R is a straight or branched $C_{1-4}$ alkyl, ester, or carboxylic acid, $R_1$ is a straight or branched $C_{1-5}$ alkyl, aralkyl, or substituted aralkyl, $R_2$ is H, alkyl, alkoxy, halogen, or mercapto, $R_4$ is H, alkyl or halogen, and the ring Z is a 5-8-membered ring containing carbon and optionally at least one nitrogen, sulfur or oxygen.

The preferred alkyl group is methyl or ethyl. The preferred halogen is either Cl or Br. The most preferred phenol is unsubstituted phenol, i.e., $C_6H_5OH$.

Preferably, $R_2$ is alkyl, alkoxy, or halogen. Preferably, the alkyl is methyl, ethyl, or propyl. Preferably, the alkoxy is methoxy, or exthoxy. Preferably, the halogen is chlorine, bromine, or iodine.

When the hydrolysis is done in one-pot, the phenol and the acid are mixed with a mixture having the compound of formula 4. Optionally, the mixture having the compound of formula 4 can be cooled prior to the addition of the acid and phenol. Preferably, the mixture is cooled to a temperature of about 50° C. to about 0° C., and more preferably to about 30° C. to about 25° C.

The combination of the compound of formula 4, the phenol, and the acid provides a second mixture, wherein the phenol preferably plays the role of a scavenger of impurities such as N-benzylated pregabalin of the following formula.

Preferably, the acid is a strong mineral acid, and more preferably hydrochloric acid, sulfuric acid, or poly phosphoric acid. As used herein, unless otherwise defined, a "strong" mineral acid is one that, when dissolved in aqueous media, produces a pH of less than about 1.5.

The second mixture also comprises an inorganic salt, such as sodium chloride, potassium chloride, magnesium sulfate, and sodium sulfate. The use of such a salt allows one to heat the second mixture to high temperatures, leading to a shorter reaction time. Preferably, second mixture is heated to a temperature of about 60° C. to about 130° C., and more preferably about 80° C. to about 110° C.

Typically, the second mixture is heated for a period of time sufficient to obtain an (S)-pregabalin salt. Preferably, the mixture is heated for about 5 to about 24 hours.

The reaction time is also related to the kind of mineral acid that is used. Preferably, the mixture is heated for about 18 to about 24 hours when the mineral acid is hydrochloric acid and for about 5 to about 10 hours when the mineral acid is sulfuric acid.

Typically, the acid protonates the amine group of (S)-Pregabalin, thus providing an acid salt of (S)-Pregabalin, from which free (S)-Pregabalin is recovered by extractions and reaction with a base. The recovery typically comprises: adding an inorganic base to the second mixture; extracting the acid salt of (S)-Pregabalin from the mixture with a $C_{4-8}$ alcohol; adjusting the pH of the extract to about 4 to about 7 and thereby precipitate (S)-Pregabalin. The precipitated (S)-Pregabalin is then collected. Preferably, the inorganic base is added to the second mixture in an amount sufficient to adjust the pH of the combination to about 1 to about 3. Preferably, the inorganic base is sodium hydroxide. Preferably, the pH of the extract is adjusted to about 4 to about 7 by adding a base. Preferably, the base is an organic base and more preferably tributylamine. Preferably, the $C_{4-8}$ alcohol is iso-butanol.

The (S)-Pregabalin obtained by the above-described process has a purity of at least about 80% area by HPLC, preferably at least about 98% area by HPLC, and more preferably about 99% to about 100% area by HPLC. The (S)-Pregabalin obtained by the above-described process also has less than 0.15%, preferably, less than 0.1%, more preferably less than 0.06%, even more preferably less than 0.02% and most preferably less than 0.01% area by HPLC of the N-benzylated pregabalin impurity.

Having described the invention with reference to certain preferred embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

Infrared Spectroscopy

Infrared spectroscopy of the compound of formula 5 was performed with a Nicolet Avatar 370 DTGS system over a range of 4000-400 cm⁻, using KBR pellets.

Example 1

Preparation of (3S)-5-methyl-3-(2-oxo-2{[(1S)-1-phenylethyl]amino}ethyl) hexanoic acid (the Precursor to Compound 1)

A three-necked flask equipped with an addition funnel, thermometer pocket, drying tube and a mechanical stirrer, was charged with toluene (400 ml), (S) (−)-phenylethylamine (142.35 g, 1.1764 mole), and 4-dimethylaminopyridine (0.7176 g, 0.0059 mole). The mixture was cooled to a temperature of −10° C. to −15° C., followed by addition of a solution of 3-isobutyl glutaric anhydride (100 g, 0.59 mole) in toluene (100 ml), over a period of 45-60 minutes, and stirring for additional 1.5-2 hours, at a temperature of −10° C. to −15° C. The mixture was then extracted with 10% aqueous solution of NaOH (500 ml), and the aqueous phase was washed with toluene (1×250 ml). The pH of the aqueous phase was adjusted to 2-2.5 by adding a solution of hydrochloric acid (1-12N). The aqueous phase was further extracted with toluene (1×800 ml) at a temperature of 70-80° C. The toluene layer was washed with 10% sodium chloride solution {700 ml) at a temperature of 70-80° C. followed by crystallization to obtain 125 g (73.0% yield) of a white solid of (3S)-5-methyl-3-(2-oxo-2-{[(1S)-1-phenylethyl]amino}ethyl) hexanoic acid with an optical purity of 99.75% area, as measured by chiral HPLC.

Example 2

Preparation of (3S)-5-methyl-3-(2-oxo-2{[(1S)-1-phenylethyl]amino}ethyl) hexanoic acid (the Precursor to Compound 1)

A three-necked flask equipped with an addition funnel, thermometer pocket, drying tube and a mechanical stirrer, was charged with toluene (800 ml), (S) (−)-phenylethylamine (284.7 g, 2.353 mole), and 4-dimethylaminopyridine (1.435 g, 0.0118 mole). The mixture was cooled to a temperature of −10° C. to −15° C., followed by addition of a solution of 3-isobutyl glutaric anhydride (200 g, 1.176 mole) in toluene (200 ml), over a period of 45-60 minutes, and stirring for additional 1.5-2 hours, at a temperature of −10° C. to −15° C. The mixture was then extracted with 10% aqueous solution of NaOH (1000 ml), and the aqueous phase was washed with toluene (1×500 ml). The pH of the aqueous phase was adjusted to 2-2.5 by adding a solution of hydrochloric acid (1-12N). The aqueous phase was further extracted with toluene (1×1600 ml) at a temperature of 70-80° C. The toluene layer was washed with 10% sodium chloride solution {1400 ml) at a temperature of 70-80° C. followed by crystallization to get 257 g (75.0% yield) of a white solid of (3S)-5-methyl- 3-(2-oxo-2-{[(1S)-1-phenylethyl]amino}ethyl) hexanoic acid with an optical purity of 99.8% area, as measured by chiral HPLC.

Example 3

Preparation of (R)-3-isobutylpentanedioic acid amide-((S)-1-phenylethyl)amide (Compound 3)

A three-necked flask equipped with an addition funnel, thermometer pocket, drying tube and a mechanical stirrer, was charged with methylene dichloride (1000 ml), (3S)-5-methyl-3-(2-oxo-2{[(1S)-1-phenylethyl]amino}ethyl) hexanoic acid (200 g, 0.687 mole), and with triethylamine (7.65 g, 0.756 mole), and cooled to 0°-5° C. followed by addition of ethyl chloroformate (90 g, 0.825 mole). The mixture was stirred for 1-2 hours at a temperature of 20° C. to 25° C., followed by quenching with 25% aqueous ammonia (1000 ml). The resulted slurry was filtered and washed with water and dried to get 140 g (70.0% yield) of a white solid of (R)-3-isobutylpentanedioic acid amide-((S)-1-phenylethyl)amide of formula 3, with a purity of 95% area, as measured by HPLC.

Example 4

Preparation of (R)-3-isobutylpentanedioic acid amide-((S)-1-phenylethyl)amide (Compound 1)

A three-necked flask equipped with an addition funnel, thermometer pocket, drying tube and a mechanical stirrer, was charged with methylene dichloride (500 ml), (3S)-5-methyl-3-(2-oxo-2{[(1S)-1-phenylethyl]amino}ethyl)hexanoic acid (100 g, 0.343 mole), and with triethylamine (41.67 g, 0.412 mole), and cooled to −15° C. to −20° C. followed by addition of ethyl chloroformate (39.1 g, 0.36 mole). The mixture was stirred for 1-2 hours at a temperature of −15° C. to −20° C., followed by quenching over a solution of 20% aqueous ammonia (280 ml). The dichloromethane was distilled out from the mass followed by filtering the resulted slurry, washed with water and dried to get 87 g (87% yield) of a white solid of (R)-3-isobutylpentanedioic acid amide-((S)-1-phenylethyl)amide of formula 1, with a purity of 98% area, as measured by HPLC.

Example 5

Preparation of (R)-3-isobutylpentanedioic acid amide-((S)-1-phenylethyl) amide (Compound 1)

A three-necked flask equipped with an addition funnel, thermometer pocket, drying tube and a mechanical stirrer, was charged with methylene dichloride (125 ml), (3S)-5-methyl-3-(2-oxo-2{[(1S)-1-phenylethyl]amino}ethyl) hexanoic acid (25 g, 0.086 mole), triethyl amine (10.43 g, 0.129 mole), and cooled to 0°-5° C. followed by addition of pivaloyl chloride (12.43 g, 0.103 mole). The mixture was stirred for 1-2 hours at a temperature of 20° C. to 25° C., followed by quenching with 20% aqueous ammonia (250 ml). The resulted slurry was filtered and washed with water and dried to get 15.2 g (61% yield) of a white solid of (R)-3-isobutylpentanedioic acid amide-((S)-1-phenylethyl)amide of formula 1, with a purity of 95% area, as measured by HPLC.

Example 6

Preparation of (R)-3-isobutylpentanedioic acid amide-((S)-1-phenylethyl) amide (Compound 1)

A three-necked flask equipped with an addition funnel, thermometer pocket, drying tube and a mechanical stirrer, was charged with acetone (125 ml), (3S)-5-methyl-3-(2-oxo-2{[(1S)-1-phenylethyl]amino}ethyl) hexanoic acid (25 g, 0.086 mole), triethyl amine (10.43 g, 0.129 mole), and cooled to 0-5° C. followed by addition of pivaloyl chloride (12.43 g, 0.103 mole). The mixture was stirred for 1-2 hours at a temperature of 20° C. to 25° C., followed by quenching with 20% aqueous ammonia (250 ml). The resulted slurry was filtered and washed with water and dried to get 10.68 g (43.4% yield) of a white solid of (R)-3-isobutylpentanedioic acid amide-((S)-1-phenylethyl)amide of formula 1, with a purity of 95.4% area, as measured by HPLC.

Example 7

Preparation of {(S)-4-methyl-2-[((S)-1-phenylethyl-carbamoyl)-methyl]pentyl}carbamic acid methyl ester (Compound 4)

A three-necked flask equipped with an addition funnel, thermometer pocket, drying tube and a mechanical stirrer, was charged with methanol (2000 ml), (R)-3-isobutylpentanedioic acid amide-((S)-1-phenylmethyl) amide, compound of formula 1 (200 g, 0.689 mole) and cooled to 0° to 5° C. followed by addition of sodium methoxide (149 g, 2.758 mole). The reaction mass was cooled to −15 to −25° C. followed by addition of bromine (165.5 g, 1.034 mole) and stirred for 1-2 h at −15 to −25° C. The mixture was gradually warmed to a temperature of 0° C. and then to 55-65° C., followed by stirring for 1 to 2 hours. The solvent was then stripped off and water was added to the mass. The resulted slurry was further extracted with toluene, toluene layer washed with brine followed by stripping off the solvent results in 215 g (97% yield) of {(S)-4-methyl-2-[((S)-1-phenylethylcarbamoyl)-methyl]pentyl}carbamic acid methyl ester (4) with a purity of 90.9% area, as measured by HPLC.

Example 8

Preparation of {(S)-4-methyl-2-[((S)-1-phenylethyl-carbamoyl)-methyl]pentyl}carbamic acid methyl ester (Compound 4)

A three-necked flask equipped with an addition funnel, thermometer pocket, drying tube and a mechanical stirrer, was charged with methanol (1000 ml), (R)-3-isobutylpentanedioic acid amide-((S)-1-phenylmethyl) amide, compound of formula 1 (50 g, 0.1724 mole) and cooled to 0° to 5° C. followed by addition of sodium hydroxide (27.58 g, 0.6896 mole). The reaction mass was cooled to −15 to −25° C. followed by addition of bromine (41.38 g, 0.2586 mole) and stirred for 1-2 h at −15 to −25° C. The mixture was gradually warmed to a temperature of 0° C. and then to 55-65° C., followed by stirring for 1 to 2 hours. The solvent was then stripped off and water was added to the mass. The resulted slurry was further extracted with toluene, toluene layer washed with brine followed by stripping off the solvent results in 53 g (96% yield) of {(S)-4-methyl-2-[((S)-1-phenylethylcarbamoyl)-methyl]pentyl}carbamic acid methyl ester (4) with a purity of 92.89% area, as measured by HPLC.

Example 9

Preparation of {(S)-4-methyl-2-[((S)-1-phenylethyl-carbamoyl)-methyl]pentyl}carbamic acid methyl ester (Compound 4)

A three-necked flask equipped with an addition funnel, thermometer pocket, drying tube and a mechanical stirrer, was charged with acetone (25 ml), (3S)-5-methyl-3-(2-oxo-2{[(1S)-1-phenylethyl]amino}ethyl) hexanoic acid (5 g, 0.0172 mole), and with triethylamine (2.17 g, 0.0215 mole), and cooled to −10° to −20° C. followed by addition of solution of ethyl chloroformate (2.05 g, 0.0189 mole in 5 ml acetone). The mixture was stirred for 1 hour at a temperature of −10° to −20° C., followed by addition of solution of sodium azide (2.8 g, 0.0429 mole in water). The resulted slurry was maintained for 1 hour at −10° to −20° C., quenched over ice water followed by extracting the mass with sufficient amount of toluene. The toluene layer was slowly added over a refluxing mixture of toluene and methyl alcohol, followed by stirring for 2 to 4 hours. The stripping off the solvent results in 4.95 g (89.7% yield) of {(S)-4-methyl-2-[((S)-1-phenylethylcarbamoyl)-methyl]pentylcarbamic acid methyl ester (120) with a purity of 97.4% area, as measured by HPLC.

Example 10

Preparation of (S)-Pregabalin

A three-necked flask equipped with an addition funnel, thermometer pocket, drying tube and a mechanical stirrer, was charged with methanol (2000 ml), (R)-3-isobutylpentanedioic acid amide-((S)-1-phenylmethyl) amide, compound of formula 1 (200 g, 0.689 mole) and cooled to 0° to 5° C. followed by addition of sodium methoxide (149 g, 2.758 mole). The reaction mass was cooled to −15 to −25° C. followed by addition of bromine (165.5 g, 1.034 mole) and stirred for 1-2 h at −15 to −25° C. The mixture was gradually warmed to a temperature of 0° C. and then to 55-65° C., followed by stirring for 1 to 2 hours. The solvent was then stripped off and water was added to the mass. The resulted slurry was further extracted with toluene, toluene layer washed with brine followed by stripping off the solvent. 4N hydrochloric acid (2580 ml), phenol (10.72 g, 0.114 mole), sodium chloride (78.15 g, 1.342 mole) was added to the mass and was heated to 105°-110° C. for 15-24 hours, and then cooled to room temperature, i.e., about 20° to about 25° C. An aqueous 40% sodium hydroxide solution was added in an amount sufficient to provide a pH of 1. The solution was then extracted with 600 ml of iso-butanol, the organic layer was separated, and Bu3N was added in an amount sufficient to provide a pH of 4. The (S)-Pregabalin was precipitated, filtered, and washed with 100 ml of iso-butanol which on crystallization from isobutanol water mixture results in (S)-Pregabalin as white crystals in a 56% yield. Purity: 99.85% area by HPLC. N-benzylated pregabalin: 0.01% area by HPLC.

Example 11

Preparation of (S)-Pregabalin

A three-necked flask equipped with an addition funnel, thermometer pocket, drying tube and a mechanical stirrer, was charged with methanol (500 ml), (R)-3-isobutylpentanedioic acid amide-((S)-1-phenylmethyl) amide, compound of formula 1 (25 g, 0.086 mole) and cooled to 0° to 5° C. followed by addition of sodium hydroxide (13.79 g, 0.3448 mole). The reaction mass was cooled to −15 to −25° C. followed by addition of bromine (20.69 g, 0.129 mole) and stirred for 1-2 h at −15 to −25° C. The mixture was gradually warmed to a temperature of 0° C. and then to 55-65° C., followed by stirring for 1 to 2 hours. The solvent was then stripped off and water was added to the mass. The resulted slurry was further extracted with toluene, toluene layer washed with brine followed by stripping off the solvent. 4N hydrochloric acid (300 ml), phenol (1.1 g, 0.0117 mole), sodium chloride (16.04 g, 0.2741 mole) was added to the mass and was heated to −105°-110° C. for 15-24 hours, and then cooled to room temperature, i.e., about 20° to about 25° C. An aqueous 40% sodium hydroxide solution was added in an amount sufficient to provide a pH of 1. The solution was then extracted with 600 ml of iso-butanol, the organic layer was separated, and Bu3N was added in an amount sufficient to provide a pH of 4. The (S)-Pregabalin was precipitated, filtered, and washed with 100 ml of iso-butanol which on crystallization from isobutanol water mixture results in (S)-Pregabalin as white crystals in 52.7% yield. Purity: 99.95% area by HPLC. N-benzylated pregabalin: 0.02% area by HPLC.

Example 12

Preparation of (S)-Pregabalin

A three-necked flask equipped with an addition funnel, thermometer pocket, drying tube and a mechanical stirrer, was charged with methanol (500 ml), (R)-3-isobutylpentanedioic acid amide-((S)-1-phenylmethyl) amide, compound of formula 1 (25 g, 0.086 mole) and cooled to 0° to 5° C. followed by addition of sodium hydroxide (13.79 g, 0.3448 mole). The reaction mass was cooled to −15 to −25° C. followed by addition of bromine (20.69 g, 0.129 mole) and stirred for 1-2 h at −15 to −25° C. The mixture was gradually warmed to a temperature of 0° C. and then to 55-65° C., followed by stirring for 1 to 2 hours. The solvent was then stripped off followed by addition of 4N hydrochloric acid (300 ml), phenol (1.83 g, 0.0194 mole), sodium chloride (16.04 g, 0.2741 mole) and was heated to 105°-115° C. for 15-24 hours, and then cooled to room temperature, i.e., about 20° to about 25° C. An aqueous 40% sodium hydroxide solution was added in an amount sufficient to provide a pH of 1. The solution was then extracted with 150 ml of iso-butanol, the organic layer was separated, and Bu3N was added in an amount sufficient to provide a pH of 4. The (S)-Pregabalin was precipitated, filtered, and washed with 100 ml of iso-butanol which on crystallization from isobutanol water mixture results into (S)-Pregabalin as white crystals in a 53.86% yield. Purity: 99.94% area by HPLC. N-benzylated pregabalin: 0.01% area by HPLC.

Example 13

Preparation of (S)-Pregabalin

A three-necked flask equipped with an addition funnel, thermometer pocket, drying tube and a mechanical stirrer, was charged with methanol (2000 ml), (R)-3-isobutylpentanedioic acid amide-((S)-1-phenylmethyl) amide, compound of formula 1 (200 g, 0.689 mole) and cooled to 0° to 5° C., followed by addition of sodium methoxide (149 g, 2.758 mole). The reaction mass was cooled to −15 to −25° C., followed by addition of bromine (165.5 g, 1.034 mole) and was stirred for 1-2 h at −15 to −25° C. The mixture was gradually warmed to a temperature of 0° C. and then to 55-65° C., followed by stirring for 1 to 2 hours. The solvent was stripped off and then 4N hydrochloric acid (2580 ml), phenol (10.72 g, 0.114 mole), and sodium chloride (78.15 g, 1.342 mole) were added to the mass, followed by heating to 105°-110° C. for 15-24 hours, and then cooling to room temperature, i.e., about 20° to about 25° C. An aqueous 40% sodium hydroxide solution was added in an amount sufficient to provide a pH of 1. The solution was then extracted with 600 ml of iso-butanol, and the organic layer was separated. Bu3N was added in an amount sufficient to provide a pH of 4. The crude (S)-Pregabalin was precipitated, filtered, and washed with 100 ml of iso-butanol providing (S)-Pregabalin with purity of 95.87% area by HPLC.

Example 14

Preparation of (S)-Pregabalin

A three-necked flask equipped with an addition funnel, thermometer pocket, drying tube and a mechanical stirrer, was charged with acetone (200 ml), (3S)-5-methyl-3-(2-oxo-2{[(1S)-1-phenylethyl]amino}ethyl) hexanoic acid compound (50 g, 0.172 mole), and with triethylamine (21.7 g, 0.215 mole), and cooled to −10° to −20° C. followed by addition of solution of methyl chloroformate (18.67 g, 0.196 mole in 50 ml acetone). The mixture was stirred for 1 hour at a temperature of −10° to −20° C., followed by addition of solution of sodium azide (27.92 g, 0.429 mole in water). The resulted slurry was maintained for 1 hour at −10° to −20° C., quenched over ice water followed by extracting the mass with sufficient amount of toluene. The toluene layer was slowly added over a refluxing mixture of toluene and methyl alcohol, followed by stirring for 2 to 4 hours followed by stripping of solvents results into an oily mass. 4N hydrochloric acid (600 ml), phenol (2.42 g, 0.0257 mole), sodium chloride (40.2 g, 0.687 mole) was added to the oily mass and was heated to 105°-110° C. for 15-24 hours, and then cooled to room temperature, i.e., about 20° to about 25° C. An aqueous 40% sodium hydroxide solution was added in an amount sufficient to provide a pH of 1. The solution was then extracted with 150 ml of iso-butanol, the organic layer was separated, and Bu3N was added in an amount sufficient to provide a pH of 4-4.5. The (S)-Pregabalin was precipitated, filtered, and washed with 25 ml of iso-butanol which on crystallization from isobutanol water mixture resulted in (S)-Pregabalin as white crystals in a 67% yield. Purity: 99.9% area by HPLC.

Example 15

Preparation of (S)-Pregabalin

A three-necked flask equipped with an addition funnel, thermometer pocket, drying tube and a mechanical stirrer, was charged with acetone (200 ml), (3S)-5-methyl-3-(2-oxo-2{[(1S)-1-phenylethyl]amino}ethyl) hexanoic acid (50 g, 0.172 mole), and with triethylamine (21.7 g, 0.215 mole), and cooled to −10° to −20° C. followed by addition of solution of methyl chloroformate (18.67 g, 0.196 mole in 50 ml acetone). The mixture was stirred for 1 hour at a temperature of −10° to −20° C., followed by addition of solution of sodium azide (27.92 g, 0.429 mole in water). The resulting slurry was maintained for 1 hour at −10° to −20° C., quenched over ice water followed by extracting the mass with sufficient amount of toluene. The toluene layer was slowly added over a refluxing mixture of toluene and methyl alcohol, followed by stirring for 2 to 4 hours followed addition of 4N hydrochloric acid (600 ml), phenol (2.42 g, 0.0257 mole), sodium chloride (40.2 g, 0.687 mole) was added to the mass and was heated to 105°-110° C. for 15-24 hours, and then cooled to room temperature, i.e., about 20° to about 25° C. An aqueous 40% sodium hydroxide solution was added in an amount sufficient to provide a pH of 1. The solution was then extracted with 150 ml of iso-butanol, the organic layer was separated, and Bu3N was added in an amount sufficient to provide a pH of 4-4.5. The (S)-Pregabalin was precipitated, filtered, and washed with 25 ml of iso-butanol which on crystallization from isobutanol water mixture results in (S)-Pregabalin as white crystals in a 65% yield. Purity: 99.98% area by HPLC, N-benzylated pregabalin: 0.01% area by HPLC.

Example 16

One Pot Preparation of (S)-Pregabalin from (R)-3-isobutylpentanedioic acid amide-((S)-1-phenylmethyl) amide A three-necked flask equipped with an addition funnel, thermometer pocket, drying tube and a mechanical stirrer, was charged with methanol (2000 ml), (R)-3-isobutylpentanedioic acid amide-((S)-1-phenylmethyl) amide, compound of formula 1 (50 g, 0.172 mole) and cooled to 0° to 5° C. followed by addition of sodium methoxide (37.25 g, 0.689 mole). The reaction mass was cooled to −15 to −25° C. followed by addition of bromine (41.4 g, 0.258 mole) and stirred for 1-2 h at −15 to −25° C. The mixture was gradually warmed to a temperature of 0° C. and then to 55-65° C., followed by stirring for 1 to 2 hours. The reaction was cooled to 25-30° C. followed by addition of 4N hydrochloric acid (600 ml), phenol (2.42 g, 0.026 mole), sodium chloride (10.1 g, 0.1724 mole). The mass was heated to 105°-110° C. for 15-24 hours, and then cooled to room temperature, i.e., about 20° to about 25° C. An aqueous 40% sodium hydroxide solution was added in an amount sufficient to provide a pH of 1. The solution was then extracted with 300 ml of iso-butanol, the organic layer was separated, and Bu3N was added in an amount sufficient to provide a pH of −4-5. The (S)-Pregabalin was precipitated, filtered, and washed with 100 ml of iso-butanol which on crystallization from isobutanol water mixture results in (S)-Pregabalin as white crystals in a 46% yield. Purity: 100% area by HPLC.

Example 17

One Pot Preparation of (S)-Pregabalin from (R)-3-isobutylpentanedioic acid amide-((S)-1-phenylmethyl) amide A three-necked flask equipped with an addition funnel, thermometer pocket, drying tube and a mechanical stirrer, was charged with methanol (1000 ml), (R)-3-isobutylpentanedioic acid amide-((S)-1-phenylmethyl) amide, compound of formula 1 (50 g, 0.172 mole) and cooled to 0° to 5° C. followed by addition of sodium hydroxide (27.52 g, 0.688 mole). The reaction mass was cooled to −15 to −25° C. followed by addition of bromine (41.38 g, 0.258 mole) and stirred for 1-2 h at −15 to −25° C. The mixture was gradually warmed to a temperature of 0° C. and then to 55-65° C., followed by stirring for 1 to 2 hours. The reaction was cooled to 25-30° C. followed by addition of 4N hydrochloric acid (600 ml), phenol (2.42 g, 0.026 mole), sodium chloride (10.1 g, 0.1724 mole). The mass was heated to 105°-110° C. for 15-24 hours, and then cooled to room temperature, i.e., about 20° to about 25° C. An aqueous 40% sodium hydroxide solution was added in an amount sufficient to provide a pH of 1. The solution was then extracted with 300 ml of iso-butanol, the organic layer was separated, and Bu3N was added in an amount sufficient to provide a pH of 4-5. The (S)-Pregabalin was precipitated, filtered, and washed with 100 ml of iso-butanol which on crystallization from isobutanol water mixture results in (S)-Pregabalin as white crystals in a 59.5% yield. Purity: 99.44% area by HPLC. N-benzylated pregabalin: 0.06% area by HPLC.

Example 18

Conversion of the Compound of Formula 4 to (S)-Pregabalin: Example 14 of International Publication No. WO 2007/035890

A 0.21 reactor was loaded with 70% sulfuric acid (200 g) containing compound 26 (10 g, 0.031 mole), and was heated to 115-120° C. for 5-10 hours, and then cooled to room temperature, i.e., about 20° to about 25° C. An aqueous 40% sodium hydroxide solution was added in an amount sufficient to provide a pH of 1. The solution was then extracted with 35 ml of iso-butanol, the organic layer was separated, and Bu3N was added in an amount sufficient to provide a pH of 4. The (S) Pregabalin was precipitated, filtered, and washed with 10 ml of iso-butanol. After drying at 55° C. under vacuum, (S)-Pregabalin was obtained as white crystals in a 40.4% yield. Purity: 99.95% area by HPLC.

Compound 26 has the following chemical structure:

wherein Ar is a $C_{6-10}$ aromatic group, and R is a straight or branched $C_{1-4}$ alkyl, ester or carboxylic acid.

Example 19

Conversion of the Compound of Formula 4 to (S)-Pregabalin: Example 16 of International Publication No. WO 2007/035890

A flask was loaded with 47% HBr (12 ml), water (6 ml), and compound 26 (6 g), and then was heated to reflux for 3 hours. The solution was cooled to room temperature, and water (12 ml) was added. An aqueous 47% sodium hydroxide solution was added to obtain pH of 3. The solution was then extracted twice with isobutanol (15 ml), the combined organic layers were evaporated and fresh isobutanol was added (15 ml). Bu3N (3.8 g) was added. The mixture was cooled to 2° C. for 1 hour, then (S)-Pregabalin was filtered, and washed with of iso-butanol (3 ml). After drying at 55° C. under vacuum, (S)-Pregabalin was obtained as white crystals in a 90% yield.

Example 20

Preparation of (S)-Pregabalin

A three-necked flask equipped with an addition funnel, thermometer pocket, drying tube and a mechanical stirrer, was charged with methanol (2000 ml), (R)-3-isobutylpentanedioic acid amide-((S)-1-phenylmethyl) amide, compound of formula 1 (200 g, 0.689 mole) and cooled to 0° to 5° C., followed by addition of sodium methoxide (149 g, 2.758 mole). The reaction mass was cooled to −15 to −25° C., followed by addition of bromine (165.5 g, 1.034 mole) and was stirred for 1-2 h at −15 to −25° C. The mixture was gradually warmed to a temperature of 0° C. and then to 55-65° C., followed by stirring for 1 to 2 hours. The solvent was stripped off and then 4N hydrochloric acid (2580 ml), and sodium chloride (78.15 g, 1.342 mole) were added to the mass, followed by heating to 105°-110° C. for 15-24 hours, and then cooling to room temperature, i.e., about 20° to about 25° C. An aqueous 40% sodium hydroxide solution was added in an amount sufficient to provide a pH of 1. The solution was then extracted with 600 ml of iso-butanol, which on crystallization from isobutanol water mixture resulted in (S)-Pregabalin as white crystals in a 64.9% yield; Purity 99.68% area by HPLC, N-benzylated pregabalin: 0.13% area by HPLC.

We claim:

1. A compound of the following formula 5 wherein Ar is a $C_{6-10}$ aromatic group, and R is a straight or branched $C_{1-4}$ alkyl, ester, or carboxylic acid.

2. The compound of claim 1, wherein the compound is isolated.

3. The compound of claim 1, wherein the $C_{6-10}$ aromatic group is naphthyl, phenyl, substituted phenyl, or substituted naphthyl.

4. The compound of claim 1, wherein the $C_{1-4}$ alkyl is methyl, ethyl, isopropyl, n-butyl, isobutyl, or t-butyl.

5. The compound of claim 1, wherein Ar is phenyl and R is ethyl.

6. A process for preparing (S)-Pregabalin comprising a) preparing the compound formula 5 of claim 1 by reacting a compound of formula 3 with an azide nucleophile to obtain compound of formula 5 b) converting the compound of formula 5 to (S)-Pregabalin, wherein Ar is a $C_{6-10}$ aromatic group, and R is a straight or branched $C_{1-4}$ alkyl, ester, or carboxylic acid, and X is a leaving group.

7. A process for preparing (S)-Pregabalin via the compound of claim 1 comprising:
   a) reacting the compound of formula 5 of claim 1 to produce a compound of formula 4;
   b) combining the compound of the following formula 4 with an acid and a phenol of formula 2;

c) recovering (S)-Pregabalin,
   wherein Ar is a $C_{6-10}$ aromatic group, R is a straight or branched $C_{1-4}$ alkyl, ester, or carboxylic acid, $R_1$ is a straight or branched $C_{1-5}$ alkyl, aralkyl, or substituted aralkyl, $R_2$ is H, alkyl, alkoxy, halogen, or mercapto, $R_4$ is H, alkyl or halogen, and the ring Z is a 5-8-membered ring containing carbon and optionally at least one nitrogen, sulfur or oxygen.

8. The process of claim 7, wherein the $C_{6-10}$ aromatic group is naphthyl, phenyl, substituted phenyl, or substituted naphthyl.

9. The process of claim 7, wherein the $C_{1-4}$ alkyl is methyl, ethyl, isopropyl, n-butyl, isobutyl, or t-butyl.

10. The process of claim 7, wherein the ester is a $C_{2-4}$ ester.

11. The process of claim 7, wherein the carboxylic acid is a $C_{1-2}$ carboxylic acid.

12. The process of claim 7, wherein the $C_{1-5}$ alkyl is methyl.

13. The process of claim 7, wherein the aralkyl is a $C_{7-10}$ aralkyl.

14. The process of claim 7, wherein the acid is a strong mineral acid.

15. The process of claim 14, wherein the strong mineral acid is hydrochloric acid, sulfuric acid, or polyphosphoric acid.

16. The process of claim 7, wherein the phenol of formula 2 is an unsubstituted phenol.

17. The process of claim 7, wherein the compound of formula 4, the acid, and the phenol are combined in the presence of an inorganic salt.

18. The process of claim 17, wherein the inorganic salt is sodium chloride, potassium chloride, magnesium sulfate, and sodium sulfate.

19. The process of claim 7, wherein the combination of the compound of formula 4, the phenol, and the acid is heated to obtain a salt of (S)-pregabalin.

20. The process of claim 19, wherein the combination is heated to a temperature of about 60° C. to about 130° C.

21. The process of claim 19, wherein the (S)-Pregabalin is recovered by a process comprising:
    i) adding an inorganic base to the combination;
    ii) extracting the salt of (S)-Pregabalin from the mixture with a $C_{4-8}$ alcohol;
    iii) adjusting the pH of the extract to about 4 to about 7 and precipitate (S)-Pregabalin; and
    iv) collecting the precipitated (S)-Pregabalin.

22. The process of claim 21, wherein the inorganic base in step i) is added in an amount sufficient to adjust the pH of the combination to about 1 to about 3.

23. The process of claim 21, wherein the inorganic base is sodium hydroxide.

24. The process of claim 21, wherein the pH is adjusted in step iii) by adding a base.

25. The process of claim 24, wherein the base is an organic base.

26. The process of claim 25, wherein the organic base is tributylamine.

27. The process of claim 21, wherein the $C_{4-8}$ alcohol is iso-butanol.

28. The process of claim 7, wherein the (S)-Pregabalin has less than 0.15% area by HPLC of N-benzylated pregabalin.

29. The process of claim 7, wherein the compound of formula 4 is prepared by a process comprising combining a compound of formula 1 with bromine and a base in a straight or branched alkyl alcohol.

30. The process of claim 29, wherein the straight or branched alkyl alcohol is methyl, ethyl, isopropyl, n-butyl, isobutyl, or t-butyl alcohol.

31. The process of claim 29, wherein the base that is combined with the compound of formula 1 and the bromine is a metal alkoxide or a metal hydroxide.

32. The process of claim 31, wherein the metal alkoxide is a $C_{1-4}$ alkoxide.

33. The process of claim 29, wherein the base that is combined with the compound of formula 1 and the bromine is sodium hydroxide or potassium hydroxide.

34. The process of claim 29, wherein the combination of the compound of formula 1, the bromine, the base, and the alcohol is heated to obtain the compound of formula 4.

35. The process of claim 34, wherein the combination of the compound of formula 1, the bromine, the base, and the alcohol is heated to a temperature of about 50° C. to about 70° C.

36. The process of claim 29, wherein the compound of formula 4 is converted to (S)-Pregabalin without isolation.

37. The process of claim 7, wherein the compound of formula 4 is prepared by a process comprising: (i) combining a compound of formula 3 with an azide nucleophile to obtain a compound of formula 5, and (ii) combining the compound of formula 5 with an alcohol to obtain the compound of formula 4, wherein X is a leaving group.

38. The process of claim 37, wherein the leaving group is a halogen or a mixed anhydride.

39. The process of claim 37, wherein the azide nucleophile is $NaN_3$, diphenylphosphoryl azide, trialkyl silyl azide, or trialkyl tin azide.

40. The process of claim 37, wherein the compound of formula 3 is combined with the azide nucleophile at a temperature of about 30° C. to about −30° C.

41. The process of claim 37, wherein the organic solvent is selected from the group consisting of aromatic hydrocarbons, aliphatic hydrocarbons, ethers and ketones.

42. The process of claim 37, wherein the organic solvent is acetone or toluene.

43. The process of claim 37, wherein the compound of formula 5 is recovered prior to combination with the alcohol.

44. The process of claim 43, wherein the compound of formula 5 is recovered by extraction.

45. The process of claim 37, wherein the alcohol is a $C_{1-5}$ alcohol.

46. The process of claim 37, wherein the alcohol is methanol, ethanol, isopropanol, t-butanol, n-butanol or isobutanol.

47. The process of claim 37, wherein the compound of formula 5 is added to the alcohol while heating the alcohol.

48. The process of claim 47, wherein the alcohol is heated to a temperature of about 50° C. to about 110° C.

49. The process of claim 37, wherein the compound of formula 4 is converted to (S)-Pregabalin without isolation.

* * * * *